United States Patent [19]

Harreus et al.

[11] Patent Number: 5,684,200
[45] Date of Patent: Nov. 4, 1997

[54] PROCESS FOR THE PREPARATION OF HYDROXYLAMINE ETHERS AND THEIR SALTS AND INTERMEDIATES FOR THIS PURPOSE

[75] Inventors: Albrecht Harreus, Ludwigshafen; Norbert Goetz, Worms; Volker Maywald, Ludwigshafen; Harald Rang, Altrip; Ulf Misslitz, Neustadt; Ulrich Klein, Limburgerhof, all of Germany

[73] Assignee: BASF Aktiengesellschaft, Ludwigshafen, Germany

[21] Appl. No.: 454,371

[22] PCT Filed: Dec. 17, 1993

[86] PCT No.: PCT/EP93/03597

§ 371 Date: Jun. 6, 1995

§ 102(e) Date: Jun. 6, 1995

[87] PCT Pub. No.: WO94/14757

PCT Pub. Date: Jul. 7, 1994

[30] Foreign Application Priority Data

Dec. 29, 1992 [DE] Germany .................. 42 44 390.3

[51] Int. Cl.$^6$ .............. C07C 209/62; C07C 251/54; C07C 253/30; C07C 255/62
[52] U.S. Cl. .............. 564/256; 558/422; 564/353
[58] Field of Search .............. 564/256, 353; 558/422

[56] References Cited

U.S. PATENT DOCUMENTS

| | | | |
|---|---|---|---|
| 3,723,429 | 3/1973 | Mamalis et al. | 260/249.9 |
| 3,845,126 | 10/1974 | Giraudon et al. | 564/256 |
| 4,150,043 | 4/1979 | Gebert et al. | 206/348.44 |
| 4,404,384 | 9/1983 | Gebert et al. | 544/394 |
| 4,647,698 | 3/1987 | Henrick | 564/256 |
| 5,190,573 | 3/1993 | Misslitz et al. | 504/292 |

FOREIGN PATENT DOCUMENTS

| | | |
|---|---|---|
| 23560 | 2/1981 | European Pat. Off. . |
| 4204203 | 2/1992 | Germany . |
| 4204206 | 2/1992 | Germany . |
| 3258757 | 11/1991 | Japan . |

OTHER PUBLICATIONS

Houben–Weyl, Methoden der organischen Chemie, vol. E16a, 4th Edition, 1990, pp. 214–250.
Bioorg. Khim., vol. 12, 1986, pp. 1662–1675.
Heterocycles, vol. 20, No. 5, 1983, Bajwa et al., pp. 839–843.
J. Am. Chem. Soc., vol. 74, 1952, pp. 3956–3957.
J. of Agric. and Food Chem., vol. 38, 1990, pp. 514–520.

Primary Examiner—Peter O'Sullivan
Attorney, Agent, or Firm—Keil & Weinkauf

[57] ABSTRACT

Hydroxylamine ethers I

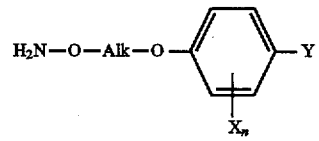

(where X is $NO_2$, CN, halogen, alkyl or haloalkyl, Y is H, $NO_2$, CN, halogen, alkyl or haloalkyl, n is 0–2 or 1–4 where Y and all radicals X are halogen and Alk is unsubstituted or substituted alkylene) and their salts with mineral acids or strong organic acids are prepared by reacting either a hydroximino compound II

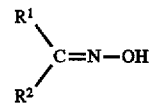

(where $R^1$ is alkyl, $R^2$ is alkyl or alkoxy or $R^1+R^2$ form an alkylene chain) in the presence of an alkali metal hydroxide, alkali metal alcoholate, alkali metal bicarbonate or alkali metal carbonate as the base, or the corresponding anion II directly, with an alkylating agent III

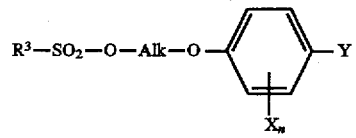

(where $R^3$ is unsubstituted or substituted alkyl or unsubstituted or substituted phenyl) to give an oximino derivative IV

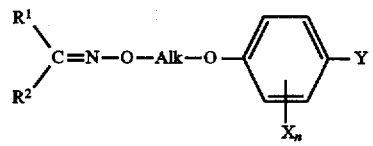

said derivative is cleaved by means of a mineral acid or a strong organic acid to give the salt of I and, if desired, the latter is converted by means of a base into the free compound I.

The hydroxylamine ethers I are intermediates for crop protection agents and drugs.

9 Claims, No Drawings

PROCESS FOR THE PREPARATION OF HYDROXYLAMINE ETHERS AND THEIR SALTS AND INTERMEDIATES FOR THIS PURPOSE

This application is a 371 of PCT/EP93/03597, filed Dec. 17, 1993.

The present invention relates to a process for the preparation of hydroxylamine ethers of the formula I

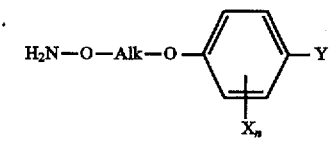

in which the variables have the following meaning:

X is nitro, cyano, halogen, $C_1-C_4$-alkyl and $C_1-C_4$-haloalkyl,

Y is hydrogen, nitro, cyano, halogen, $C_1-C_4$-alkyl and $C_1-C_4$-haloalkyl, n is 0-2 or 1-4 where Y and all radicals X are halogen and Alk is a $C_2$- or $C_3$-alkylene chain which, if desired, may carry from one to three $C_1-C_3$-alkyl groups, and their salts with mineral acids or strong organic acids.

The present invention furthermore relates to novel oximino derivatives of the formula IVa

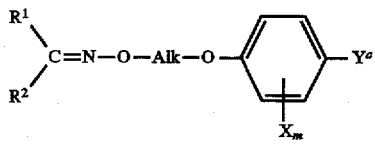

in which the variables have the following meaning:

$R^1$ is $C_1-C_4$-alkyl, $R^2$ is $C_1-C_4$-alkyl or $C_1-C_6$-alkoxy or $R^1$ and $R^2$ together form $C_4-C_6$-alkylene, X is nitro, cyano, halogen, $C_1-C_4$-alkyl or $C_1-C_4$-haloalkyl, $Y^a$ is hydrogen, nitro, cyano or halogen, m is 0–2 when Y is nitro, cyano or halogen, 1 when Y is hydrogen and X is nitro, cyano or $C_1-C_4$-alkoxy and 2 or 3 when Y is hydrogen, and Alk is a $C_2$- or $C_3$-alkylene chain which, if desired, may carry from one to three $C_1-C_3$-alkyl groups, and, when $R^1$ and $R^2$ are both methyl, Alk is —(CH$_2$)$_3$— and $X_n$ is 2,5—Cl$_2$, Y cannot be chlorine.

The preparation of the compounds I cannot be carried out by direct O-alkylation of hydroxylamine but requires the use of methods involving protective groups. Such methods for the synthesis of hydroxylamine ethers of the type comprising the compounds I are described, for example, in Houben-Weyl, Methoden der organischen Chemie, Volume E16a, 1990, page 214 et seq. This publication also discloses the so-called N-hydroxyphthalimide method, by means of which hydroxylamine ethers of the type of the compounds I have been prepared to date according to EP-A 456 112, DE-A 42 04 203 and DE-A 42 04 206. However, this method has disadvantages for industrial use. Thus, the elimination of the protective group results not only in the desired O-substituted hydroxylamines but as a rule also in useless coupling products, for example phthalic hydrazide in the cleavage with hydrazine. Recovery of the protective group used is usually also impossible.

J. Agric. Food Chem. 38 (1990), 514 discloses the preparation of acetone O-[3-(4-phenoxyphenoxy)propyl]-oxime in the presence of potassium tert-butylate in dioxane as a solvent. However, the process described is not suitable for an industrial preparation of the oximino derivatives IV, since large amounts of solvents are consumed. A corresponding reaction with smaller amounts of solvents is impossible since in this case viscous emulsions are obtained.

A further publication (J. Am. Chem. Soc. 74 (1952), 3956) describes the condensation of, inter alia, 2-phenoxyethyl bromide with the sodium salt of acetone oxime (although no information is given concerning the process conditions) and the cleavage of the resulting oxime ether with hydrochloric acid.

In DE-A 26 51 083, DE-A 26 51 085 and JP-A91/258 757, relatively expensive bases which are technically difficult to handle, such as alkali metal hydrides, for example sodium hydride, alkali metal amides, for example sodium amide, or organometallic compounds, for example butyllithium, are used in alkylation reactions with hydroximino derivatives of the type comprising the compounds II. These reactions must be carried out under anhydrous conditions, which is technically complicated.

Some of the oximino derivatives IV have already been disclosed in U.S. Pat. No. 4,647,698 (cf. formula (B) of the patent), as pesticides. The patent states that sodium hydride is present as the base for the preparation of said oximino derivatives from hydroximino compounds II and alkylating agents of the type comprising the compounds III. The disadvantage here is the technically complicated procedure under an inert gas.

According to Bioorg. Khim. 12 (1986), 1662, 1-(1-ethoxyethylideneaminoxy)-2-phenoxyethane can be obtained by reacting 1-(1-ethoxyethylideneaminoxy)-2-bromoethane with sodium phenolate in methanol. However, the disadvantage here is that the first-mentioned reactant is obtainable in a yield of only 28% and that the product itself is formed in a yield of only 40%.

Furthermore, it can be taken from EP-A 023 560 that certain ketoximes can be reacted with (cyclo)alkyl or arylalkyl halides to give O-substituted ketoximes. The publication does not mention the use of sulfonic esters of the type comprising the compounds III as alkylating agents.

Regarding the hydrolysis of oximino derivatives IV in which $R^2$ is $C_1-C_4$-alkyl, the literature gives only a few similar examples. Thus, Bajwa et al., Heterocycles 20 (1983), 839, obtained the corresponding hydroxylamine ethers I in the form of the hydrochloride in the hydrolysis of a compound of the formula IV, where $R^1$ and $R^2$ are each methyl, Alk is 1,3-propylidene, Y is chlorine and $X_2$ is 2,5-dichloro, in a mixture of hydrochloric acid, ethanol and water.

It was an object of the present invention to make the hydroxylamine ethers I more readily available.

Accordingly, a process for the preparation of the hydroxylamine ethers I and their salts with mineral acids or strong organic acids has been found, wherein either a hydroximino compound of the formula II

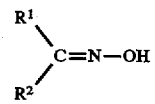

where $R^1$ is $C_1-C_4$-alkyl, $R^2$ is $C_1-C_4$-alkyl or $C_1-C_6$-alkoxy or $R^1$ and $R^2$ together form a $C_4-C_6$-alkylene chain, in the presence of an alkali metal hydroxide, alkali metal alcoholate, alkali metal bicarbonate or alkali metal carbonate as the base, or the corresponding anion of II directly, is reacted with an alkylating agent of the formula III

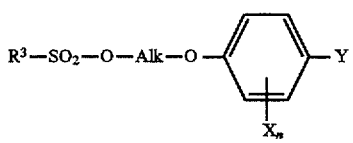

where $R^3$ is $C_1$–$C_4$-alkyl, $C_1$–$C_4$-haloalkyl or unsubstituted or substituted phenyl, to give an oximino derivative of the formula IV

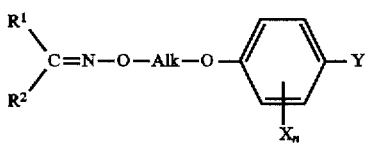

said derivative IV is then cleaved by means of a mineral acid or a strong organic acid to give the corresponding salt of I and, if desired, the latter is converted by means of a base into the free compound I.

Furthermore, novel oximino derivatives of the formula IVa have been found.

The radicals $R^1$, $R^2$, X, Y and Alk have the following specific meanings:

$R^1$ is $C_1$–$C_4$-alkyl, such as methyl, ethyl, n-propyl, 1-methylethyl, n-butyl, 1-methylpropyl, 2-methylpropyl and 1,1-dimethylethyl, preferably methyl, ethyl, n-propyl, n-butyl and 1-methylethyl, in particular methyl and ethyl, $R^2$ is methyl, ethyl, n-propyl, 1-methylethyl, n-butyl, 1-methylpropyl, 2 -methylpropyl, 1,1 -dimethylethyl or methoxy, ethoxy, n-propoxy, 1-methylethoxy, n-butoxy, 1-methylpropoxy, 2-methylpropoxy, 1,1-dimethylethoxy, n-pentyloxy, 1-methylbutoxy, 2-methylbutoxy, 3methylbutoxy, 2,2-dimethylpropoxy, 1-ethylpropoxy, n-hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy 1-ethyl-1-methylpropoxy, 1-ethyl-2-methylpropoxy, preferably methyl, ethyl, n-propyl, n-butyl and methoxy, ethoxy, n-propoxy and n-butoxy, in particular methyl, ethyl, methoxy and ethoxy, or $R^1$ and $R^2$ together form a $C_4$–$C_6$-alkylene chain, such as —$CH_2CH_2CH_2CH_2$—, —$CH_2CH_2CH_2CH_2CH_2$— or —$CH_2CH_2CH_2CH_2$—$CH_2CH_2$—, X is nitro, cyano, fluorine, chlorine, bromine and iodine, in particular fluorine and chlorine, $C_1$–$C_4$-alkyl, such as methyl, ethyl, n-propyl, 1-methylethyl, n-butyl, 1-methylpropyl, 2-methylpropyl or 1,1-dimethylethyl, preferably methyl, ethyl, n-propyl or n-butyl, in particular methyl or ethyl, or $C_1$–$C_4$-haloalkyl, in particular fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably trifluoromethyl, difluoromethyl and fluoromethyl, Y is hydrogen, nitro, cyano, fluorine, chlorine, bromine and iodine, in particular fluorine and chlorine, $C_1$–$C_4$-alkyl as stated for X, preferably methyl, ethyl, n-propyl or n-butyl, in particular methyl or ethyl, $C_1$–$C_4$-haloalkyl, in particular $C_1$- or $C_2$-haloalkyl as stated for X, preferably trifluoromethyl, difluoromethyl and fluoromethyl, and Alk is 1,2-ethylene or 1,3-propylene, both of which may be unsubstituted or may carry from one to three $C_1$–$C_3$-alkyl groups, such as methyl, ethyl, n-propyl and 1-methylethyl, preferably methyl and ethyl, in particular methyl.

$R^1$ and $R^2$ are each very particularly preferably $C_1$–$C_4$-alkyl.

Among the novel oximino derivatives IVa, particularly preferred ones are those in which $R^1$ is $C_1$–$C_4$-alkyl, preferably methyl, ethyl, n-propyl or isopropyl, in particular methyl or ethyl, $R^2$ is $C_1$–$C_4$-alkyl, preferably methyl, ethyl, n-propyl or isopropyl, in particular methyl or ethyl, or $C_1$–$C_4$-alkoxy, preferably methoxy, ethoxy, n-propoxy or isopropoxy, in particular methoxy or ethoxy, X is halogen, in particular fluorine or chlorine, $Y_a$ is hydrogen or halogen, preferably fluorine or chlorine, in particular chlorine, m is 0 or 1 when Y is halogen or 2 when Y is hydrogen, in particular 0, and Alk is a 1,2-ethylene or 1,3-propylene chain which carries one or two methyl and/or ethyl groups.

The hydroximino compounds II are commercially available in some cases or may be prepared by methods known from the literature (cf. for example U.S. Pat. No. 4,743,701).

The alkylating agents III are known in some cases or can be prepared by methods known from the literature.

The two equations below show schematically one of the possible synthesis routes for the preparation of compounds III starting from phenoxyalkanoic acids or their esters. By reaction with suitable reducing agents, for example lithium aluminum hydride or sodium borohydride, in an inert solvent, such as tetrahydrofuran, phenoxyalkanols V [cf. for example J. Pharmacol. Chemother. 7 (1952), 197] are obtained:

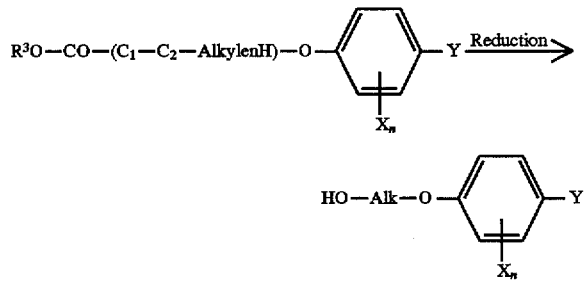

\*) Unsubstituted or substituted by $C_1$–$C_3$—alkyl groups;
$R^3$ = hydrogen or lower alkyl The phenoxyalkanols V can then be converted into the alkylating agents III by reaction with inorganic or organic acid halides. For example, the exchange of hydroxyl for $CH_3$—$SO_2$—O— is effected with methanesulfonyl chloride in the presence of a tertiary amine:

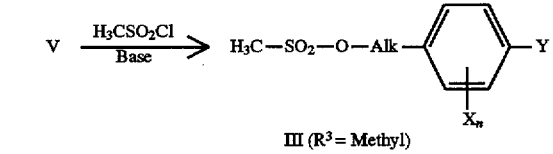

If the hydroxyl group of the phenoxyalkanols V is replaced by chlorine, bromine (for exemple by means of phosphorus tribromide in the presence of a tertiary amine) or iodine, the halogenated alkylating agent VI

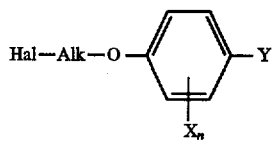

where Hal is chlorine, bromine or iodine, which may be used instead of the alkylating agents III, are obtained.

Specifically, the reaction of II with III is carried out as follows:

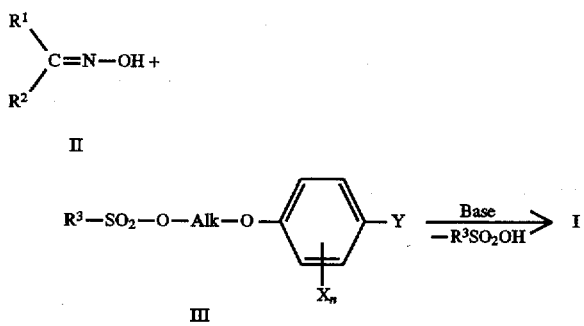

Usually, the reaction temperature is from 20° to 150° C., preferably from 40° to 120° C., in particular from 60° to 100° C.

Examples of suitable bases are alkali metal hydroxides, such as sodium hydroxide and potassium hydroxide, alkali metal alcoholates, such as lithium methylate, sodium methylate, potassium methylate, lithium ethylate, sodium ethylate, potassium ethylate, sodium tert-butylate and potassium tert-butylate, alkali metal carbonates, such as sodium carbonate and potassium carbonate, and alkali metal bicarbonates, such as sodium bicarbonate and potassium bicarbonate.

The abovementioned sodium compounds, in particular sodium hydroxide and sodium methylate, are particularly preferred.

The base is expediently used in an equivalent amount, based on the compound II.

Regarding the definition of dipolar aprotic solvents, reference may be made to Chr. Reichardt, Lösungsmittel-Effekte in der organischen Chemie, Verlag Chemie 1969. Dipolar aprotic solvents are to be understood in particular as meaning those solvents which are not hydrogen bridge donors and have a pronounced dipole moment ($\mu$ greater than 2.5 Debye) and a high dielectric constant ($\epsilon$ greater than 15).

Examples of suitable dipolar aprotic solvents are sulfoxides, such as dimethyl sulfoxide, diethyl sulfoxide, dimethyl sulfone, diethyl sulfone, methyl ethyl sulfone, tetramethylene sulfone; nitriles, such as acetonitrile, benzonitrile, butyronitrile, isobutyronitrile, m-chlorobenzonitrile; N,N-disubstituted carboxamides, such as dimethylformamide, N,N-dimethylbenzamide, N,N-dimethylacetamide, N,N-dimethylphenylacetamide, N,N-dimethylcyclohexanecarboxamide, N,N-dimethylpropionamide, and homologous carboxylic acid piperidide, carboxylic acid morpholide, carboxylic acid pyrrolidide; corresponding N,N-diethyl-, N,N-di-n-propyl-, N,N-diisopropyl-, N,N-diisobutyl-, N,N-dibenzyl-, N-methyl-N-phenyl- and N-cyclohexyl-N-methylcarboxamides, N-methylformanilide; N-alkyllactams, such as N-ethylpyrrolidone, N-octylpyrrolidone, N-cyclohexylpyrrolidone, N-methylpyrrolidone, N-butylpyrrolidone; tetrasubstituted cyclic and acyclic ureas, such as tetramethylurea, tetrabutylurea, 1,3-dimethyl-2-imidazolinone, 1,3-dimethyl-3,4,5,6-tetrahydro-2(1H)-pyrimidone, and mixtures of the stated solvents. N,N-Dialkyl-substituted carboxamides, such as dimethylformamide and dimethylacetamide, or N-alkyl-substituted lactams, such as N-methylpyrrolidone, are preferred.

The solvent or solvent mixture is used in general in an amount of from 0.3 to 1.0 l, preferably from 0.4 to 0.8 l, in particular from 0.5 to 0.7 l, per mol of hydroximino compound II.

The starting materials II and III are used in general in equimolar amounts but, in order to optimize the yield, it may be advantageous to employ II in an excess of from 0.1 to 0.5, preferably from 0.2 to 0.4, in particular from 0.2 to 0.3, mol equivalent, based on III.

After the end of the reaction, the predominant part of the solvent used can be recovered by means of distillation under reduced pressure. After water has been added to the residue at room temperature, the products IV can be isolated, if desired by extraction with, for example, hydrocarbons, such as toluene and cyclohexane. If the oximino derivatives IV are to be prepared in pure form, the crude products may be purified in a conventional manner, for example by crystallization or fractional distillation under reduced pressure.

For the reaction itself, it is advantageous first to prepare a solution of the hydroximino compound II, to add the base, then to bring this mixture to the reaction temperature, to stir the mixture for some time to the salt formation and then to add the alkylating agent III, if desired in solution.

Before the addition of the alkylating agent III, it may be advantageous to separate off, by incipient distillation under reduced pressure, the alcohol liberated by the salt formation or the water liberated. This is very particularly advisable when alkylating agents VI are used instead of III.

The hydroximino compound of the formula II may furthermore be converted into its alkali metal salt in a preliminary step and, if desired, isolated as such. The solvent chosen for the reaction is then added to this and the reaction with the alkylating agent III is carried out without further auxiliary bases. The abovementioned alkali metal carbonates, bicarbonates, hydroxides and alcoholates are advantageously suited for this purpose. These are reacted in conventional solvents, for example in alcohols, or in water, in stoichiometric amounts, with the relevant hydroximino compound II at from 0° to 50° C. The use of sodium methylate solution, with or without the addition of a hydrocarbon, such as toluene, has proven useful here. After stirring for a short time (10–60 minutes), the readily volatile components are expediently removed, usually under reduced pressure. The residue contains the alkali metal salt of II.

Although the oximino derivatives IV can in principle also be prepared from II, or from the corresponding anion of II, and an alkylating agent VI, the alkylating agents III have proven particularly useful. Here, $R^3$ is preferably $C_1$–$C_4$-alkyl, $C_1$–$C_4$-haloalkyl, phenyl or phenyl which is monosubstituted to trisubstituted by halogen and/or $C_1$–$C_4$-alkyl. $CH_3$—$SO_2$—O—, $C_6H_5$—$SO_2$—O—, (4—$CH_3$—$C_6H_4$)—$SO_2$—O— or [2,4,6—$(CH_3)_3$—$C_6H_2$]—$SO_2$—O— are very particularly preferred.

In the case of those hydroximino compounds II in which $R^2$ is $C_1$–$C_6$-alkoxy, it is particularly advantageous that, when alkali metal alcoholates are used as bases, the alcohol liberated by salt formation at the beginning of the reaction or during the reaction may remain in the reaction mixture. Undesirable side reactions, such as the elimination of $R^3$—$SO_2$—OH or ether formation between the alcohol and III, are thus very greatly suppressed.

On the other hand, in the case of other hydroximino compounds II in which $R^2$ is $C_1$-$C_6$-alkyl, the use of alkali metal hydroxides as bases and N-alkylpyrrolidones, preferably N-methylpyrrolidone, as solvents is particularly ticularly advantageous since, in these cases, the water liberated by salt formation at the beginning of the reaction or during the reaction may remain in the reaction mixture. In this procedure, undesirable secondary reactions, such as the elimination of $R^3$—$SO_2$—OH or the hydrolysis of the alkylating agent III, are very greatly suppressed.

The corresponding hydroxylamine ether of the formula I may be liberated from IV and IVa by acidic hydrolysis. I is obtained initially in the form of the salt of the acid used and can be isolated as such or, after the addition of a base, as the free hydroxylamine ether I.

Mineral acids, preferably hydrochloric acid and phosphoric acid and strong organic acids, such as trichloroacetic acid and trifluoroacetic acid, have proven suitable for the cleavage. Those oximino derivates IV and IVa in which $R^2$ is $C_1$-$C_4$-alkyl can be particularly advantageously cleaved with mineral acids.

A very particularly preferred mineral acid is hydrochloric acid to which, if desired, a cosolvent may be added. Examples of suitable cosolvents are alcohols.

The cleavage usually takes place at a sufficient rate at from 50° to 120° C.

The amount of acid is not critical. At least an equivalent amount, based on IV or IVa, of acid is required for complete hydrolysis. In general, from 1 to 10 mol of acid per mole of IV or, if IV is not isolated, per mole of II or III are generally sufficient. A larger amount of acid is also possible but usually has no advantages.

Oximino derivatives of the formula IV where $R^1$ is methyl and $R^2$ is ethoxy may also be hydrolyzed by a method similar to that stated in DE-A 26 51 083.

As a rule, all stated process steps can be carried out at atmospheric pressure or at the autogenous pressure of the particular system.

In the present process, the hydroxylamine ethers I are obtainable in a technically simple manner. The fact that further useful products, ie. the secondary products of the protective group moiety (ketones or esters), are obtained in addition to the hydroxylamine ethers I in the cleavage of the oximino derivatives IV is particularly advantageous here. In many cases, it is even possible to recover the protective group and reuse it for the preparation of the hydroximino compounds II. Thus, for example, where $R^1$ and $R^2$ are each methyl, the acetone formed in the hydrolysis can be recycled for the preparation of further acetone oxime II (where $R^1$ and $R^2$ are each methyl).

The hydroxylamine ethers of the formula I are important intermediates for crop protection agents and drugs. As free bases or as salts, they may be condensed, for example in a manner known per se, with cyclohexanetriones or pyrones VII to give the corresponding oxime ethers VIII, which are preferably used as herbicides in crop protection (cf. for example EP-A 136 702, EP-A 142 741 and EP-A 456 112):

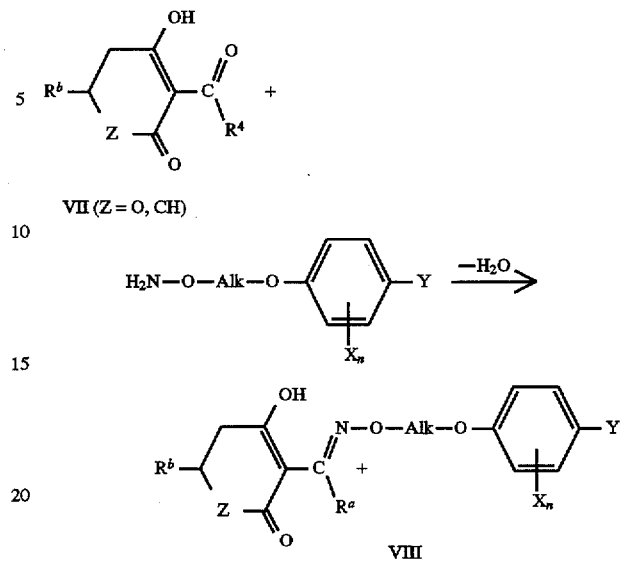

$R^a$ is preferably $C_1$-$C_4$-alkyl and $R^b$ is, for example, alkoxyalkyl, alkylthioalkyl, an unsubstituted or substituted cycloalkyl or cycloalkenyl group, an unsubstituted or substituted 5-membered heterocyclic or heteroaromatic radical, an unsubstituted or substituted 6-membered or 7-membered heterocyclic radical or an unsubstituted or substituted phenyl or pyridyl ring.

PREPARATION EXAMPLES

EXAMPLE 1

2-(4-Chlorophenoxy)-1-(1-ethoxyethylideneaminoxy)-propane (=ethyl O-[2-(4-chlorophenoxy)-propyl]-acethydroximate) (Table 1, compound No. 18)

a) Alkylation using potassium methylate as the base 105.2 g (1.5 mol) of potassium methylate were added to 155 g (1.5 mol) of ethyl acethydroximate in 1,500 ml of absolute dimethylformamide (slightly exothermic reaction). Stirring for 45 minutes at 25°–30° C. gave a clear solution, which was added in the course of 2.5 hours to a solution, at 50° C., of 265 g (1 mol) of 2-(4-chlorophenoxy)-propyl methanesulfonate in 600 ml of dimethylformamide. After the addition was complete, stirring was carried out for a further 4 hours at 50° C., after which the mixture was heated for a further hour at 100° C. and then cooled. The dimethylformamide was then removed under reduced pressure from a water pump, at a bath temperature of not more than 100° C. The residue was cooled and then taken up with 1 l of toluene and 1 l of 1% strength by weight sodium hydroxide solution. The aqueous phase was separated off and extracted once with 200 ml of toluene. The combined organic phases were washed with twice 200 ml of 1% strength by weight sodium hydroxide solution and once with water, dried and evaporated down. The crude product obtained had a purity of 94.4% (GC percent by area) and could be used directly for the further reaction (liberation of the hydroxylamine ether).

If desired, the product can be purified by means of fractional distillation at reduced pressure. Yield: 89%, bp. 100°–101° C. (at 0.2 mbar)

b) Alkylation with sodium methylate as the base 54 g of 30% strength by weight methanolic sodium methylate solution (0.3 mol of sodium methylate) were added dropwise to 30.9 g (0.3 mol) of ethyl acethydroximate in 450 ml of dimethylformamide at 50° C. The mixture obtained was stirred for a further 30 minutes, after which 180 ml of liquid were distilled off from the reaction mixture under reduced pressure at an internal temperature of not more than 50° C. 52.9 g (0.2 mol) of 2-(4-chlorophenoxy) -propyl methanesulfonate, dissolved in 70 ml of dimethylformamide, were added dropwise to the concentrate in the course of 40 minutes at the same temperature. Stirring was carried out for a further 18 hours at 50° C., after which working up was effected as described under a).

The title compound was obtained in a yield of 79%.

EXAMPLE 2

2-(4-Chlorophenoxy)-1-isopropylideneaminooxypropane (=acetone O[-2-(4-chlorophenoxy)-propyl]-oxime) (Table 1, compound No. 28)

a) Alkylation using sodium hydroxide as the base 37.4 g (0.94 mol) of sodium hydroxide were added to 68.3 g (0.94 mol) of acetone oxime and 306 ml of N-methylpyrrolidone while stirring. The mixture was heated to an internal temperature of 100° C. and 24.5 g (0.85 mol) of 2-(4-chlorophenoxy)-propyl methanesulfonate, dissolved in 155 ml of N-methylpyrrolidone, were added dropwise in the course of 45 minutes. After 2 hours, the reaction mixture was cooled to 30° C., after which 415 g of N-methylpyrrolidone were distilled off under reduced pressure at a boiling point of 46° C. (2 mbar), it being possible to recycle the N-methylpyrrolidone to the process. Thereafter, the mixture was allowed to cool, 500 ml of water were added, stirring was carried out for 45 minutes and extraction was effected with five times 250 ml of cyclohexane. The mixture was dried and evaporated down and the crude product was purified by means of fractional distillation.

The title compound was obtained in a yield of 80%; bp. 83°-87° C. (at 0.1 mbar).

b) Alkylation using the sodium salt of acetone oxime

A 30% strength by weight methanolic sodium methylate solution was diluted with 3 times the volume of toluene, after which an equivalent amount of acetone oxime was introduced. The low boilers were then removed under reduced pressure.

264.1 g (1 mol) of 2-(4-chlorophenoxy)-propyl methanesulfonate, dissolved in 180 ml of N-methylpyrrolidone, were added dropwise at 100° C. to 142.6 g (1.5 mol) of the sodium salt of acetone oxime, initially taken in 490 ml of N-methylpyrrolidone. The reaction was then allowed to continue for a further hour and the mixture was then worked up as described above.

590 ml of N-methylpyrrolidone were recovered. The yield of the title compound was 81% (purity according to GC 96%).

Table 1 shows further oximino derivatives IV and IVa which were prepared, or can be prepared, in the same manner.

EXAMPLE 3

1-Aminoxy-2-(4-chlorophenoxy)-propane (=2-(4-chlorophenoxy)-propoxyamine a) Hydrolysis of ethyl O-[2-(4-chlorophenoxy)-propyl]-acethydroximate 485 g (1.7 mol) of ethyl O-[2-(4-chlorophenoxy)-propyl] -acethydroximate (Table 1, compound No. 18; 95% pure according to GC) were added dropwise to 1.7 l (3.4 mol) of 2N hydrochloric acid at 20°-25° C. in the course of 60 minutes and the mixture was refluxed for 30 minutes. It was then cooled, brought to a pH of 10 with 280 ml of 50% strength by weight sodium hydroxide solution while cooling in an ice bath and extracted with three times 400 ml of dichloromethane. The combined organic phases were washed with water and then dried and evaporated down.

The title compound was obtained in a yield of 97% (96.9% pure according to GC analysis).

If desired, the compound can be purified by distillation; bp. 102°-104° C. (0.4 mbar).

250 MHz-$^1$H-NMR (in CDCl$_3$): δ [ppm]=1.25 (d, 3H; CH$_3$); 3.6–3.9 (m, 2H); —O—CH$_2$); 4.64 (m, 1H); Ph—O—CH(CH$_3$)); 5.5 (broad s, 2H; NH$_2$); 6.9 and 7.2 (2d, 4H); Ph-H)

b) Hydrolysis of acetone O-[2-(4-chlorophenoxy)-propyl] -oxime with trichloroacetic acid A mixture of 10 g (4.13 mmol) of acetone O-[2-(4-chlorophenoxy)-propyl]-oxime (compound 28 in Table 1) and 44 g of 30% strength by weight aqueous trichloroacetic acid solution was heated for 10 hours at 78° C. and a reduced pressure of 450 mbar in a stirred apparatus having an attached 30 cm column, 110 g of water being continuously added dropwise to the reaction mixture and the resulting water/acetone mixture being continuously distilled off. The reacted mixture was worked up by rendering it alkaline with 10% strength by weight sodium hydroxide solution and extracting it with toluene. 6 g of 2-(4-chlorophenoxy)-propoxyamine were isolated. Yield: 72%.

c) Hydrolysis of acetone O-[2-(4-chlorophenoxy)-propyl] -oxime with trifluoroacetic acid 10 g (4.13 mmol) of acetone O-[2-(4-chloro-phenoxy)-propyl]-oxime and 31 g of 30% strength aqueous trifluoroacetic acid solution were heated for 8¾ hours at 80° C. at a reduced pressure of 430 mbar, similarly to experiment 3b, 100 g of water being continuously added dropwise to the reaction mixture and a water/acetone mixture being distilled off. The working up similarly to 3b) gave 6.4 g of 2-(4-chlorophenoxy)-propoxyamine in this case. Yield: 76%.

d) Hydrolysis of acetone O-[2-(4-chlorophenoxy)-propyl] -oxime with hydrochloric acid In a stirred apparatus, 10 g (4.13 mmol) of acetone O-[2-(4-chlorophenoxy)-propyl]-oxime were dissolved in a mixture of 250 g of n-propanol, 38 g of concentrated hydrochloric acid (38% strength by weight) and 60 g of water. This solution was heated for 6 hours at 80° C. and then worked up by distilling off n-propanol and water. After recrystallization of the residue from 20% strength by weight hydrochloric acid, 7.7 g of the hydrochloride of 2-(4-chlorophenoxy)-propoxyamine were obtained. Yield: 78%.

TABLE 1

$$\begin{array}{c} R^1 \\ \phantom{R}C=N-O-Alk-O-\text{C}_6\text{H}_3(X_n)-Y \\ R^2 \end{array} \quad IV$$

| No. | $R^1$ | $R^2$ | Alk | $X_n$ | Y | Physical properties | $^1$H-NMR (in CDCl$_3$) δ[ppm] |
|---|---|---|---|---|---|---|---|
| 1 | CH$_3$ | CH$_3$ | —CH$_2$—CH$_2$— | 3-CF$_3$ | H | | 1,85–1,95(2s, 6H, CH$_3$); 4,2–4,45(2m, 4H, —CH$_2$—CH$_2$—); 7,05–7,5(m, 4H, Ph—H) |
| 2 | CH$_3$ | OC$_2$H$_5$ | —CH$_2$—CH$_2$— | — | NO$_2$ | | 1,3(t, 3H, CH$_3$); 1,93(s, 3H, CH$_3$); 4,0 (q, 2H, —O—CH$_2$); 4,25–4,35(m, 4H, —CH$_2$—CH$_2$—); 7,0 and 8,2(2d, 4H, Ph—H) |
| 3 | CH$_3$ | CH$_3$ | —CH$_2$—CH(CH$_3$)— | — | Br | | |
| 4 | CH$_3$ | OC$_2$H$_5$ | —CH$_2$—CH(CH$_3$)— | — | Br | | |
| 5 | CH$_3$ | OC$_2$H$_5$ | —CH$_2$—CH$_2$— | 2-F | F | | |
| 6 | CH$_3$ | CH$_3$ | —CH$_2$—CH(CH$_3$)— | 2-Cl | H | | |
| 7 | CH$_3$ | OC$_2$H$_5$ | —CH(—CH$_2$—)—(CH$_2$)$_2$—CH$_3$ | — | CH$_3$ | | 0,95(t, 3H, CH$_3$); 1,3(t, 3H, CH$_3$); 1,35–1,8(m, 4H); 1,85(s, 3H, CH$_3$); 2,3(s, 3H, Ph—CH$_3$); 3,9–4,2(m, 5H); 6,9–7,1(2d, 4H, Ph—H) |
| 8 | —(CH$_2$)$_5$— | | —CH$_2$—CH(CH$_3$)— | — | Cl | bp. 174° C. (0,4 mbar) | 1,24(d, 3H, CH$_3$); 1,3–1,9(m, 6H, Cyclohexyl-H); 2,1 and 2,38 (2t, 4H, Cyclohexyl-H); 4,02(m, 2H, —O—CH$_2$); 4,66(m, 1H, O—CH(CH$_3$)); 6,9–7,3(2d, 4H, Ph—H) |
| 9 | CH$_3$ | C$_2$H$_5$ | —CH$_2$—CH(CH$_3$)— | — | Cl | | |
| 10 | C$_2$H$_5$ | C$_2$H$_5$ | —CH$_2$—CH(CH$_3$)— | — | Cl | | |
| 11 | CH$_3$ | CH$_3$ | —CH$_2$—CH$_2$— | 3-Cl | H | | 1,85 und 1,9(2s, 6H, CH$_3$); 4,1 and 4,35 (2t, 4H, —CH$_2$—CH$_2$—); 6,7–7,3(m, 4H, Ph—H) |
| 12 | CH$_3$ | OC$_2$H$_5$ | —CH$_2$—CH$_2$— | 2-Cl | Cl | | 1,27(t, 3H, CH$_3$); 1,9(s, 3H, CH$_3$); 4,0 (q, 2H, —O—CH$_2$); 4,1–4,3(m, 4H, —CH$_2$—CH$_2$—); 6,8–7,4(m, 3H, Ph—H) |
| 13 | CH$_3$ | CH$_3$ | —CH$_2$—CH(CH$_3$)— | — | F | | |
| 14 | CH$_3$ | CH$_3$ | —CH$_2$—CH(CH$_3$)— | — | CN | | |
| 15 | CH$_3$ | OC$_2$H$_5$ | —CH$_2$—CH(CH$_3$)— | 2-F | H | | |
| 16 | CH$_3$ | CH$_3$ | —CH$_2$—CH(CH$_3$)— | 2-Br | 4-F | | |
| 17 | CH$_3$ | CH$_3$ | —CH$_2$—CH(CH$_3$)— | 2-Br | Cl | | |
| 18 | CH$_3$ | OC$_2$H$_5$ | —CH$_2$—CH(CH$_3$)— | — | Cl | bp. 100–101° C. (0.2 mbar) | 1,2–1,4(m, 6H, CH$_3$); 1,86(s, 3H, CH$_3$); 3,8–4,2(m, 4H, —OCH$_2$); 4,65(m, 1H, Ph—O—CH); 6,8–7,3(2m, 4H, Ph—H) |
| 19 | CH$_3$ | OC$_2$H$_5$ | —CH$_2$—CH$_2$— | 3-CF$_3$ | H | | 1,28(t, 3H, CH$_3$); 1,95(s, 3H, CH$_3$); 3,9–4,3(m, 6H); 7,0–7,45 (2m, 4H, Ph—H) |
| 20 | CH$_3$ | OCH$_3$ | —CH$_2$—CH(CH$_3$)— | — | Cl | | |
| 21 | CH$_3$ | O-iPr | —CH$_2$—CH(CH$_3$)— | — | Cl | | |
| 22 | CH$_3$ | OC$_2$H$_5$ | —(CH$_2$)$_3$— | 2-F | F | | |
| 23 | CH$_3$ | OC$_2$H$_5$ | —(CH$_2$)$_3$— | 2-Cl | Cl | | |
| 24 | CH$_3$ | OC$_2$H$_5$ | —(CH$_2$)$_3$— | — | Cl | | |
| 25 | CH$_3$ | OC$_2$H$_5$ | —(CH$_2$)$_3$— | 2-Cl | Cl | | |
| 26 | CH$_3$ | OC$_2$H$_5$ | —(CH$_2$)$_3$— | H | H | | 1,28(t, 3H, CH$_3$); 1,95(s, 3H, CH$_3$); 2,15(m, 2H); 3,9–4,2(m, 6H); 6,8–7,4 (2m, 5H, Ph—H) |
| 27 | CH$_3$ | OC$_2$H$_5$ | —(CH$_2$)$_3$— | — | F | | 1,28(t,3H, CH$_3$); 1,94(s, 3H, CH$_3$); 2,1(m, 2H); 3,9–4,2(m, 6H); 6,75–7,05 (m, 4H, Ph—H) |
| 28 | CH$_3$ | CH$_3$ | —CH$_2$—CH(CH$_3$)— | — | Cl | bp. 84–88° C. (0.1 mbar) | 1,3(d, 3H, CH$_3$); 1,78 and 1,84(2s, 6H, —CH$_3$); 4,0–4,25(m, 4H, —OCH$_2$—); 4,62 (m, 1H; Ph—O—CH); 6,88 and 7,18(2m, 4H, Ph—H) |
| 29 | CH$_3$ | CH$_3$ | —CH(CH$_3$)—CH$_2$— | — | Cl | | |
| 30 | CH$_3$ | CH$_3$ | —CH(CH$_3$)—CH(CH$_3$)— | — | Cl | | |
| 31 | CH$_3$ | OC$_2$H$_5$ | —CH$_2$—CH(CH$_3$)—CH$_2$— | — | F | | |
| 32 | CH$_3$ | OC$_2$H$_5$ | —CH$_2$—CH(CH$_3$)— | 2-CH$_3$ | Cl | | |
| 33 | CH$_3$ | OC$_2$H$_5$ | —CH$_2$—CH(CH$_3$)— | 2,5-Cl$_2$ | Cl | | |
| 34 | CH$_3$ | CH$_3$ | —CH$_2$—CH(CH$_3$)— | 2-Cl | CF$_3$ | | |
| 35 | CH$_3$ | CH$_3$ | —CH$_2$—CH(CH$_3$)— | 3-Cl | CN | | |
| 36 | CH$_3$ | OC$_2$H$_5$ | —CH$_2$—CH(C$_2$H$_5$)— | — | Cl | | |
| 37 | CH$_3$ | CH$_3$ | —CH$_2$—CH(CH$_3$)— | 3,5-(CF$_3$)$_2$ | H | | |
| 38 | CH$_3$ | CH$_3$ | —CH$_2$—CH$_2$—CH$_2$— | — | Cl | | |
| 39 | CH$_3$ | OC$_2$H$_5$ | —CH$_2$—CH(CH$_3$)— | 2-Cl | Cl | | |

TABLE 1-continued

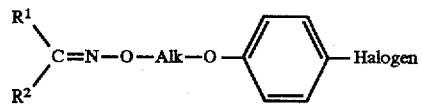

| No. | R¹ | R² | Alk | $X_n$ | Y | Physical properties | ¹H-NMR (in CDCl₃) δ[ppm] |
|---|---|---|---|---|---|---|---|
| 40 | CH₃ | OC₂H₅ | —(CH₂)₂—CH(CH₃)— | — | Cl | | |
| 41 | CH₃ | OC₂H₅ | —CH₂—CH(CH₃)— | 3-Cl | CN | | |

We claim:

1. A process for the preparation of hydroxylamine ethers of the formula I

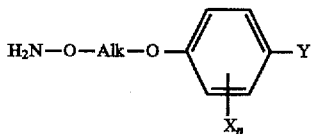

in which the variables have the following meaning:

X is nitro, cyano, halogen, $C_1$–$C_4$-alkyl and $C_1$–$C_4$-haloalkyl,

Y is hydrogen, nitro, cyano, halogen, $C_1$–$C_4$-alkyl and $C_1$–$C_4$-haloalkyl, n is 0–2 or 1–4 where Y and all radicals X are halogen and Alk is a $C_2$- or $C_3$-alkylene chain which, if desired, may carry from one to three $C_1$–$C_3$-alkyl groups, and their salts with mineral acids or strong organic acids, wherein either a hydroximino compound of the formula II

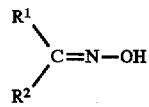

where R¹ is $C_1$–$C_4$-alkyl and R² is $C_1$–$C_4$-alkyl or $C_1$–$C_6$-alkoxy or R¹ and R² together form a $C_4$–$C_6$-alkylene chain, in the presence of an alkali metal hydroxide, alkali metal alcoholate, alkali metal bicarbonate or alkali metal carbonate as the base, or the corresponding anion of II directly, is reacted with an alkylating agent of the formula III

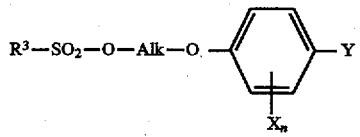

where R³ is $C_1$–$C_4$-alkyl, $C_1$–$C_4$-haloalkyl or unsubstituted or substituted phenyl, to give an oximino derivative of the formula IV

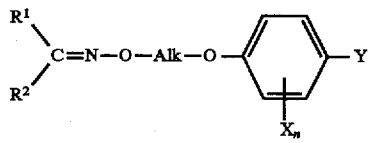

said derivative IV is then cleaved by means of a mineral acid or a strong organic acid to give the corresponding salt of I and, if desired, the latter is converted by means of a base into the free compound I.

2. A process as claimed in claim 1, wherein the reaction of II with III is carried out in from 0.3 to 1.0 l of an organic solvent per mol of II.

3. A process as claimed in claim 1, wherein the reaction of II with III is carried out in a dipolar aprotic solvent which has a large dipole moment (μ greater than 2.5 Debye) and a high dielectric constant (ε greater than 15).

4. A process as claimed in claim 1, wherein the reaction of II with III is carried out in an N,N-disubstituted carboxamide or in an N-substituted lactam.

5. A process as claimed in claim 1, wherein the reaction of II with III is carried out in the presence of sodium hydroxide, a sodium alcoholate, a potassium alcoholate, sodiumbicarbonate or sodiumcarbonate as the base.

6. A process as claimed in claim 1, wherein those compounds II in which R² is $C_1$–$C_4$-alkoxy are reacted with III in the presence of an alkali metal alcoholate as the base in an N,N-dialkyl-substituted carboxamide.

7. A process as claimed in claim 1, wherein those compounds II in which R² is $C_1$–$C_4$-alkyl are reacted with III in the presence of an alkali metal hydroxide as the base in an N-substituted 2-pyrrolidone as the solvent.

8. A process as claimed in claim 1, wherein those oximino derivatives IV in which R² is $C_1$–$C_4$-alkyl are cleaved with a mineral acid.

9. Oximino derivatives of the formula IVa

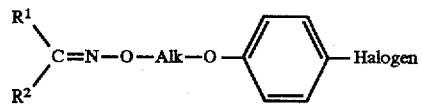

in which the variables have the following meaning:

R¹ is $C_1$–$C_4$-alkyl,

R² is $C_1$–$C_4$alkyl or $C_4$–$C_6$-alkoxy or

R¹ and R² together form $C_4$–$C_6$-alkylene,

Alk is a $C_2$- or $C_3$-alkylene chain which, if desired, may carry from one to three $C_1$–$C_3$-alkyl groups.

* * * * *

UNITED STATES PATENT AND TRADEMARK OFFICE
CERTIFICATE OF CORRECTION

PATENT NO.: 5,684,200

DATED: November 4, 1997

INVENTOR(S): HARREUS et al.

It is certified that error appears in the above-identified patent and that said Letters Patent is hereby corrected as shown below:

Column 14, claim 5, line 34, "sodiumbicarbonate or sodiumcarbonate" should be:
-- sodium bicarbonate or sodium carbonate--.

Column 14, claim 9, line 60, "$C_4$-$C_6$-alkoxy" should be --$C_1$-$C_6$-alkoxy--.

Signed and Sealed this

Fourteenth Day of July, 1998

*Attest:*

BRUCE LEHMAN

*Attesting Officer*     *Commissioner of Patents and Trademarks*